(12) United States Patent
Moser et al.

(10) Patent No.: US 11,918,797 B2
(45) Date of Patent: Mar. 5, 2024

(54) SYRINGE BODY, SYRINGE AND INJECTION DEVICE FOR INJECTING A HIGHLY VISCOUS MEDIUM

(71) Applicant: SCHOTT Pharma Schweiz AG, St. Gallen (CH)

(72) Inventors: Raymond Moser, Engelburg (CH); Tom van Ginneken, Rorschacherberg (CH); Sebastian Brechler, Flawil (CH)

(73) Assignee: SCHOTT Pharma Schweiz AG, St. Gallen (CH)

(*) Notice: Subject to any disclaimer, the term of this patent is extended or adjusted under 35 U.S.C. 154(b) by 520 days.

(21) Appl. No.: 16/750,525

(22) Filed: Jan. 23, 2020

(65) Prior Publication Data

US 2020/0246555 A1 Aug. 6, 2020

(30) Foreign Application Priority Data

Jan. 31, 2019 (EP) .................................. 19154910

(51) Int. Cl.
*A61M 5/34* (2006.01)
*A61K 31/728* (2006.01)
(Continued)

(52) U.S. Cl.
CPC .......... *A61M 5/347* (2013.01); *A61K 31/728* (2013.01); *A61M 5/3129* (2013.01); *A61M 5/3293* (2013.01)

(58) Field of Classification Search
CPC .. A61M 5/347; A61M 5/3129; A61M 5/3293; A61M 5/343; A61M 5/344; A61M 5/34
See application file for complete search history.

(56) References Cited

U.S. PATENT DOCUMENTS 3,306,291 A * 2/1967 Burke ................. A61M 5/3202
604/110
2003/0220613 A1 11/2003 Fabian et al.
(Continued)

FOREIGN PATENT DOCUMENTS

| CN | 103857429 A | * | 6/2014 | ............. A61M 5/20 |
| CN | 112386769 A | * | 2/2021 | ............. A61M 5/178 |
| EP | 3777928 B1 | * | 10/2021 | ............. A61J 1/065 |

OTHER PUBLICATIONS

Brydson, J.A. "11—Aliphatic Polyolefins other than Polyethylene, and Diene Rubbers". 1999. Accessed online at: https://doi.org/10.1016/B978-075064132-6/50052-8.*
(Continued)

*Primary Examiner* — Brandy S Lee
*Assistant Examiner* — John J Crawford
(74) *Attorney, Agent, or Firm* — Taylor IP, P.C.

(57) ABSTRACT

A syringe body for a syringe for injecting a highly viscous medium has a hollow cylindrical configuration, forms a chamber configured to receive the highly viscous medium, and includes: a distal end portion; a proximal end portion having an opening through which a piston rod arrangement is insertable into the chamber; and a Luer lock connector formed at the distal end portion, the Luer lock connector having an outer cone with a further opening configured to dispense the highly viscous medium and a sleeve-shaped portion with an inner thread. The syringe body has a minimum NPO resistance of over 90 N.

17 Claims, 3 Drawing Sheets

(51) Int. Cl.
*A61M 5/31* (2006.01)
*A61M 5/32* (2006.01)

(56) References Cited

U.S. PATENT DOCUMENTS

| | | | |
|---|---|---|---|
| 2010/0152679 A1 | 6/2010 | Tezel et al. | |
| 2011/0092916 A1* | 4/2011 | Tezel | A61M 5/347 604/241 |
| 2014/0012227 A1* | 1/2014 | Sigg | A61K 9/0048 604/218 |
| 2019/0070072 A1* | 3/2019 | Arakawa | B29C 49/06 |
| 2021/0046255 A1* | 2/2021 | Moser | A61M 5/347 |

OTHER PUBLICATIONS

ISO 80369-7. "Small-bore connector for liquids and gases in healthcare applications—Part 7: Connectors for intravascular or hypodermic applications". 2016.*
European Search Report dated May 17, 2019 for European Patent Application No. 19154910 (4 pages).
European Office Action dated Jun. 7, 2019 for European Patent Application No. 19154910 (7 pages).
Schott: "TSK HPC: Advanced hub @BULLET Advanced hub geometry @BULLET ULTRA thin wall @BULLET External threading @BULLET Hard polymer," Dec. 19, 2018 (2 pages).
"ISO 80369-7: Small-bore connectors for liquids and gases in healthcare applications—Part 7: Connectors for Intravascular or hypodermic applications," Oct. 1, 2016 (48 pages).
European Office Action dated Feb. 23, 2022 for European Patent Application No. 19 154 910.4 (11 pages).

* cited by examiner

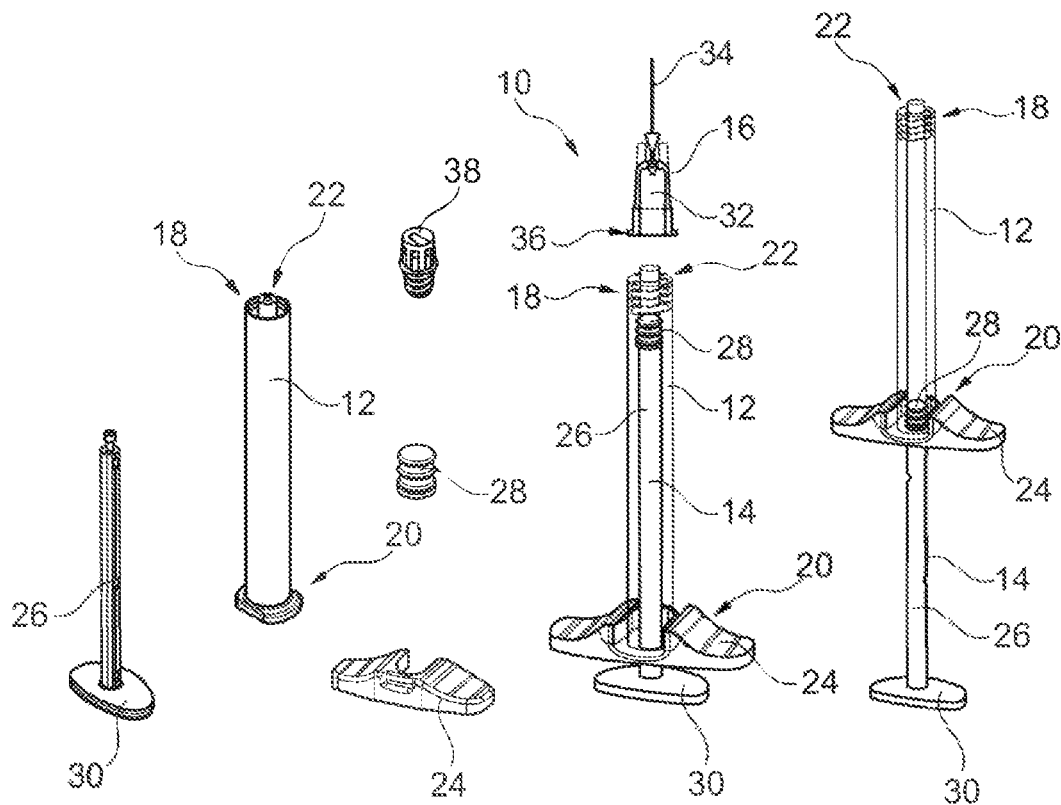
FIG. 1
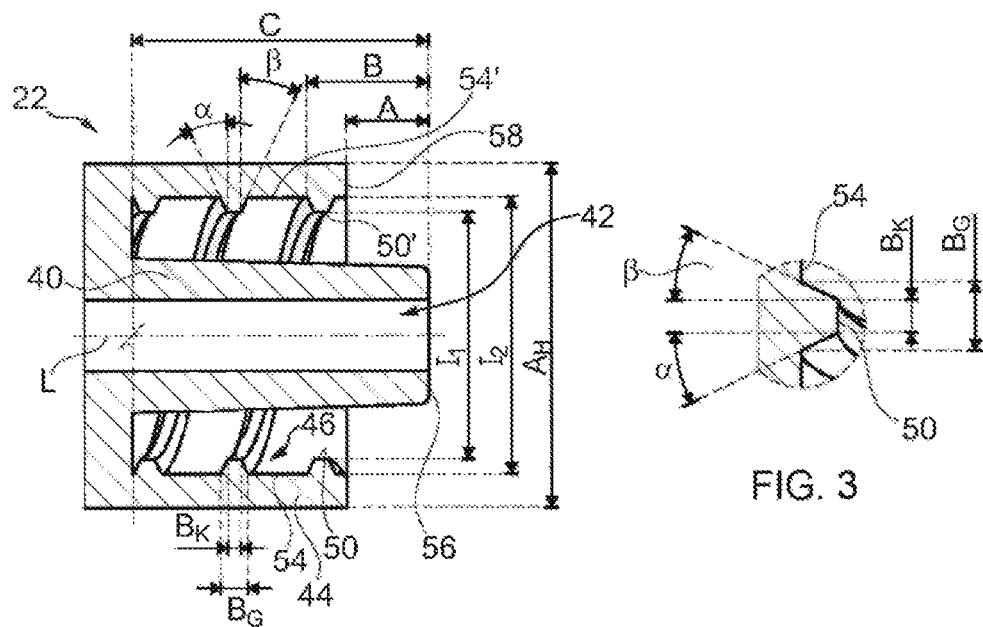
FIG. 2
FIG. 3

SYRINGE BODY, SYRINGE AND INJECTION DEVICE FOR INJECTING A HIGHLY VISCOUS MEDIUM

CROSS REFERENCE TO RELATED APPLICATIONS

This application claims priority to European Application No. 19154910.4 filed Jan. 31, 2019, the contents of which are incorporated herein by reference.

BACKGROUND OF THE INVENTION

1. Field of the Invention

The present invention relates to a syringe body, a syringe and an injection device for injecting a highly viscous medium. In particular, the syringe body, the syringe and the injection device can be used to inject or apply highly viscous pharmaceutical media.

2. Description of the Related Art

Syringes are used, for example, in the medical and cosmetic fields and serve to inject a medium contained in the syringe into the body of a patient. Thus, in the context of a cosmetic treatment of a patient's skin, for example, dermal fillers are injected beneath the surface of the patient's skin. Cosmetic applications in most cases involve the use of highly viscous media. Media received in the syringe may comprise various forms of fluids, paste, or liquid substances and mixtures.

In order to minimize the skin perforation required for the injection, and the associated pain experienced by the patient, needles with a very small cannula thickness (gauge) may be provided. This is particularly so for applications on a patient's face.

The combination of the smallest possible cannula thickness and the high viscosity of the media to be injected leads to high stresses on the syringe or the syringe body. In particular, high pressures within the syringe can lead to mechanical failure of the syringe arrangement. However, since mechanical failure of the syringe has to be avoided, the possibilities of using needles of small cannula thickness are limited in the case of previously known syringes, and this in turn brings about the above-described disadvantages for the patient.

What is needed in the art is a syringe body, a syringe and an injection device which allow needles of small cannula thickness to be used for injecting highly viscous media.

SUMMARY OF THE INVENTION

In some exemplary embodiments provided according to the present invention, a syringe body for a syringe for injecting a highly viscous medium is provided. The syringe body has a hollow cylindrical configuration, forms a chamber configured to receive the highly viscous medium, and includes: a distal end portion; a proximal end portion having an opening through which a piston rod arrangement is insertable into the chamber; and a Luer lock connector formed at the distal end portion, the Luer lock connector having an outer cone with a further opening configured to dispense the highly viscous medium and a sleeve-shaped portion with an inner thread. The syringe body has a minimum NPO resistance of over 90 N.

In some exemplary embodiments provided according to the present invention, an injection device includes: a syringe body having a hollow cylindrical configuration, forming a chamber configured to receive a highly viscous medium, and including: a distal end portion; a proximal end portion having an opening; and a Luer lock connector formed at the distal end portion, the Luer lock connector having an outer cone with a further opening configured to dispense the highly viscous medium and a sleeve-shaped portion with an inner thread, the syringe body having a minimum NPO resistance of over 90 N. A piston rod arrangement includes a piston rod and a piston mounted on a distal end of the piston rod, received in the chamber via the opening at the proximal end portion of the syringe body, and guided displaceably in the chamber.

In some exemplary embodiments provided according to the present invention, a method for performing a cosmetic procedure includes applying a highly viscous cosmetic preparation to a patient using an injection device. The injection device includes: a syringe body having a hollow cylindrical configuration, forming a chamber holding the highly viscous cosmetic preparation, and including: a distal end portion; a proximal end portion having an opening; and a Luer lock connector formed at the distal end portion, the Luer lock connector having an outer cone with a further opening configured to dispense the highly viscous cosmetic preparation and a sleeve-shaped portion with an inner thread, the syringe body having a minimum NPO resistance of over 90 N. A piston rod arrangement includes a piston rod and a piston mounted on a distal end of the piston rod, received in the chamber via the opening at the proximal end portion of the syringe body, and guided displaceably in the chamber.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 illustrates various perspective views of an an exemplary embodiment of an injection device provided according to the present invention;

FIG. 2 illustrates a sectional view of the Luer lock connector of an exemplary embodiment of a syringe body provided according to the present invention;

FIG. 3 illustrates a detail of a thread profile from FIG. 2;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 4:
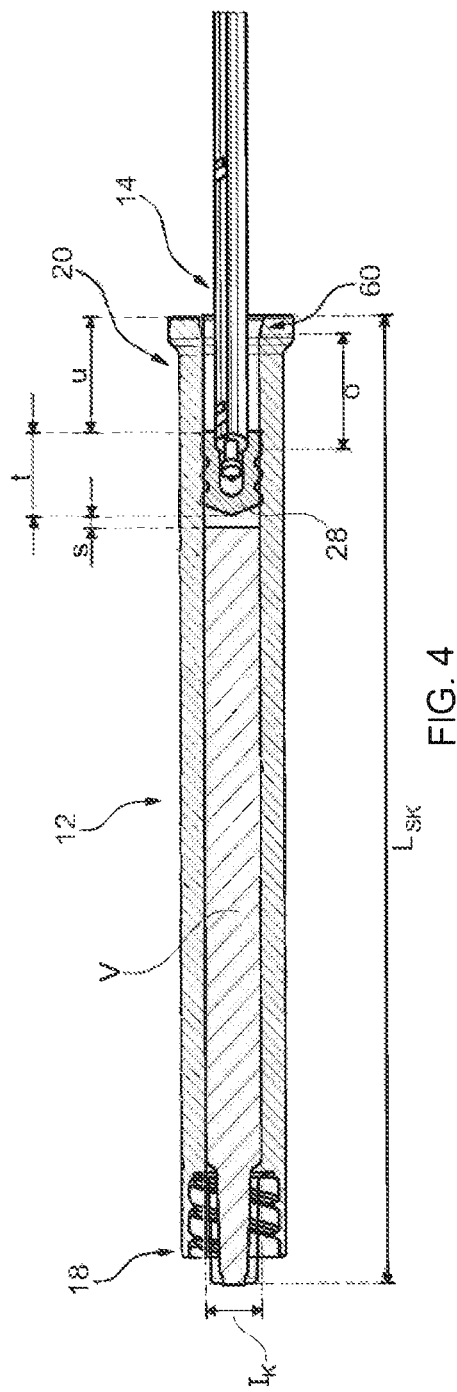
FIG. 4 illustrates a sectional view of an exemplary embodiment of a syringe body with a piston rod arrangement received therein.

One aspect of the present invention concerns a syringe body for a syringe for injecting or applying a highly viscous medium. In some embodiments, the highly viscous medium is characterized by a storage modulus G' of at least 30 Pa and at most 150 Pa, such as at least 50 Pa and at most 100 Pa, or at least 70 Pa and at most 90 Pa. The loss factor tan δ can be between 0.2 and 0.8, such as between 0.3 and 0.6 or between 0.4 and 0.5. The highly viscous medium can be a hyaluronic acid filler, for example. The viscosity can be measured with a plate/plate measurement system at 25° C. and an air pressure of 1013.25 hPa (e.g. the MCR 302 rheometer from the company Anton Paar), in particular with a frequency of 1 Hz. The measurement can be carried out, for example, by the method according to ISO 6721-10-2015-09. The syringe body comprises a distal end portion and a proximal end portion. The syringe body has a hollow cylindrical configuration and forms a chamber for receiving the highly viscous medium. The proximal end portion has an opening through which a piston rod arrangement is insertable or inserted into the chamber. The piston rod arrangement is movable in the chamber in the direction of a longitudinal axis of the chamber and is guided slidably in the syringe body.

At the distal end portion of the syringe body, a Luer lock connector is formed that comprises an outer cone, with a further opening for dispensing the highly viscous medium, and a sleeve-shaped portion with an inner thread. The Luer lock connector forms part of a Luer lock connection system and is designed to interact with a Luer lock connector counterpiece that is formed on the needle arrangement. The outer cone can also be described as a conical nozzle which protrudes beyond a distal end of the syringe body and through which the highly viscous medium can be discharged from the chamber. The outer cone likewise forms part of the Luer lock connection system and likewise interacts with a complementary counterpiece of the needle arrangement. In a Luer lock connection system, the outer cone and the sleeve-shaped portion surrounding the latter are arranged coaxially to each other. The Luer lock connector of the syringe body can be configured and dimensioned, for example, in the context of ISO 80369-7:2016-12-01. This allows exemplary embodiments of the syringe body provided according to the present invention to be used with a large number of different needle arrangements used as standard in the region of the Luer lock connection.

According to the present invention, the syringe body has a minimum NPO resistance of over 90 N. "NPO" stands for needle pop-off and denotes the abrupt detachment of a needle arrangement from a syringe body, in particular of a needle arrangement connected to the syringe body via a Luer lock connection. The minimum NPO (needle pop-off) resistance indicates a threshold value of a force which, in the context of the test procedure described further herein, is applied to a piston rod arrangement introduced into the syringe body and operatively connected to the latter. The minimum NPO resistance is defined as meaning that, below this threshold value, needle pop-off occurs in not more than 1.8% of the tested syringe bodies. At least 56 measurements of syringe bodies of the same configuration and design are needed in order to provide a meaningful result for the minimum NPO resistance. At high pressure (triggered by force applied to the syringe body via the piston rod arrangement), the needle arrangement starts to turn and comes loose from the syringe body at high speed, i.e., an inner cone of the needle arrangement complementing the outer cone of the syringe body comes loose.

The syringe body can, in some embodiments, have a minimum NPO resistance of over 95 N, such as over 100 N or over 103 N. In some embodiments, the syringe body can have a minimum NPO resistance of between 90 N and 105 N, such as of between 95 N and 103.5 N, or of between 98 N and 102 N.

In the test procedure for measuring the NPO resistance, in particular the minimum NPO resistance and the average NPO resistance, the syringe body to be tested is arranged vertically in a test machine and held in the region of the proximal end of the syringe body. The test machine used is a universal test machine "TesT 106.2 kN" from the company TesT. This, or a comparable universal test machine, is to be used for the test procedure.

The syringe body to be tested is connected via the Luer lock connector to a needle arrangement which, in order to produce the Luer lock connection by a Luer lock connector counterpiece, is screwed onto the distal end portion of the syringe body with a torque of 12 Ncm. The test procedure is intended to be carried out specifically with the needle arrangement "TSK STERiJECT hypodermic needle", ref. PRC-300131, 30 G×½, or a needle arrangement comparable thereto. The needle arrangement used for the test procedure comprises, as Luer lock connector counterpiece, an inner cone and two fins arranged on an outer circumference of a needle hub of the needle arrangement. The needle arrangement used for the test procedure comprises a cannula or hollow needle with a thickness of 30 G and a length of 13 mm (30 G×½). Before the test is carried out, the cannula is, for test purposes, flattened by a hammer and thereby closed. For the test procedure, a dry Luer lock connection is to be produced by screwing the needle arrangement onto the syringe body before then introducing a highly viscous medium into the chamber. The test procedure is carried out with non-steam-sterilized components (syringe body, needle arrangement, piston rod arrangement).

For the present test procedure, a highly viscous medium is to be chosen having a storage modulus G' of approximately 84.5 Pa and a loss factor tan δ of approximately 0.48. The viscosity can be measured with a plate/plate measurement system at 25° C. and an air pressure of 1013.25 hPa (e.g. the MCR 302 rheometer from the company Anton Paar), in particular with a frequency of 1 Hz. The measurement can be carried out, for example, by the method according to ISO 6721-10-2015-09. The syringe body to be tested is intended to be filled completely with the highly viscous material. Moreover, at the start of the test procedure, a piston rod arrangement is introduced into the syringe body and is operatively connected to the latter, although the syringe body and the piston rod arrangement are still in a starting position at the start of the test procedure, i.e., in a non-actuation position. For the present test procedure, a standard piston rod arrangement is to be used that is provided for the respective syringe body to be tested. For example, for a syringe body with an internal diameter of the chamber of 5 mm, it is possible to use a standard piston of the FM257 type (e.g. from the manufacturer Daetwyler).

By way of a test punch of the test machine, a force is applied vertically to a proximal end of the piston rod arrangement. The test punch moves at a constant test speed of 12.6 mm/min in the direction of the distal end portion of the syringe body. The force acting on the piston rod arrangement increases continuously to a maximum of 420 N. In the testing, the test punch is moved by a distance of 15 mm. The acting force is detected by a force sensor at a scanning rate of 200 Hz. The test punch is moved onwards, or the acting force increased, until leakage and/or NPO occurs, or until the maximum force of 420 N is reached. The test is stopped, i.e. leakage and/or NPO is identified, if the measured force drops suddenly by at least 30%. The acting force at the time of occurrence of leakage and/or NPO is documented and linked to the information on whether leakage and/or NPO has occurred at this force. From the documented measurement results, the previously described minimum NPO resistance and the average NPO resistance can then be determined. The leakage tested here is the leakage that occurs between the syringe body and the needle arrangement as a result of the applied force and the acting pressure. In other words, it is possible to determine the force at which the highly viscous medium undesirably escapes between the syringe body and the needle arrangement in the region of the Luer lock connection.

Mechanical failure, which is to be avoided, may be caused in particular by NPO, by leakage between interconnected syringe components, and/or by breakage of the syringe body. It has been found that, for use of highly viscous media and for a small cannula thickness of at least 31 G, it is advantageous to use a syringe body that has the minimum NPO resistance defined above. A smaller needle diameter or cannula diameter (e.g. over 30 G) means less pain for the patient than is the case with larger needle or cannula diameters (e.g. a diameter of 27 G customarily used with highly viscous media) but at the same time requires application of greater force than in the case of a larger needle or cannula diameter in order to dispense the highly viscous medium. The previously described values provided according to the present invention for the minimum NPO resistance take into account the recognition that male users correctly using a syringe or injection device may actuate the latter with a maximum force (maximum finger force) of 95 N on average. Female users correctly using a syringe or injection device may apply a maximum force (maximum finger force) of 64 N on average. The minimum NPO resistance defined previously thus represents an optimization of the syringe body structure, which ensures safe injection of a highly viscous medium with a very thin cannula but which is not overdimensioned.

In some embodiments, the syringe body has an average NPO resistance of at least 100 N, such as at least 105 N, at least 110 N, at least 115 N, or at least 117 N. In some embodiments, the average NPO resistance lies between 100 N and 120 N, such as between 105 N and 120 N, between 110 N and 120 N, or between 115 N and 117N.

The average NPO resistance indicates the mean force which, in the context of the test procedure described previously, has to be applied to a piston rod arrangement introduced into the syringe body and operatively connected to the latter, so that a needle pop-off occurs. Here too, at least 56 measurements of syringe bodies of the same configuration and design are needed in order to provide a meaningful result for the average NPO resistance.

In some embodiments, the syringe body has a minimum leakage resistance of at least 100 N. The syringe body may have a minimum leakage resistance of over 105 N, such as over 117.5 N or over 125 N. In some embodiments, the syringe body has a minimum leakage resistance of between 100 N and 130 N, such as between 105 N and 120 N or between 110 N and 115 N.

In some embodiments, the syringe body has an average leakage resistance of at least 115 N, such as at least 120 N, at least 123 N, at least 125 N, or at least 127 N. In some embodiments, the average leakage resistance lies between 110 N and 135 N, such as between 115 N and 130 N, between 120 N and 130 N, or between 125 N and 130 N.

The minimum leakage resistance indicates a threshold value of a force which, in the context of the test procedure described previously, is applied to a piston rod arrangement introduced into the syringe body and operatively connected to the latter. The minimum leakage resistance is defined as meaning that, below this threshold value, leakage occurs in less than 1.8% of the tested syringe bodies. At least 56 measurements of syringe bodies of the same configuration and design are needed in order to provide a meaningful result for the minimum leakage resistance.

Moreover, the average leakage resistance indicates the mean force which, in the context of the test procedure described previously, has to be applied to a piston rod arrangement introduced into the syringe body and operatively connected to the latter, so that leakage occurs. Here too, at least 56 measurements of syringe bodies of the same configuration and design are needed in order to provide a meaningful result for the average leakage resistance.

In some embodiments, the inner thread of the Luer lock connector can have an internal diameter of at most 7.15 mm or at most 7.12 mm. The internal diameter can be, for example, at least 7.05 mm or at least 7.08 mm. In some embodiments, the internal diameter is between 7.05 mm and 7.15 mm, such as between 7.08 mm and 7.12 mm or at most 7.1 mm. The internal diameter describes the smallest internal diameter of the sleeve-shaped end portion, i.e. measured from thread crest to opposite thread crest of the inner thread. An internal diameter of such dimensions can have a positive effect on a sufficiently tight connection between the syringe body and a needle arrangement connected thereto and can thus advantageously influence the setting of the minimum NPO resistance and of the average NPO resistance. This applies analogously in respect of the minimum leakage resistance and the average leakage resistance.

According to some embodiments of the syringe body, the inner thread, at the crest of the thread profile, can have a breadth of at least 0.44 mm or at least 0.46 mm. In some embodiments, the breadth is at most 0.52 mm or at most 0.50 mm. In some embodiments, the breadth can be between 0.44 mm and 0.52 mm, such as between 0.46 mm and 0.50 mm or 0.48 mm.

Additionally or alternatively to this, the inner thread, at the root of the thread profile, can have a breadth of at least 0.85 mm or at least 0.875 mm. In some embodiments, the breadth is at most 0.95 mm or at most 0.925 mm. In some embodiments, the breadth can be between 0.85 mm and 0.95 mm, such as between 0.875 mm and 0.925 mm, or 0.9 mm.

On both sides of the thread profile, the inner thread can have an angle of between 22.5° and 27.5°, such as an angle of 24° to 26° or of approximately 25°. The angle can be described as the angle enclosed between a line orthogonal to the longitudinal axis of the syringe body, and intersecting the thread profile, and the flank of the thread profile.

By configuring the thread profile parameters in accordance with the previously described dimensions, the contact face of the threaded connection, i.e. the contact face between the inner thread of the syringe body and a complementary outer thread of an associated needle arrangement, can be adapted. This can improve the Luer lock connection to the associated needle arrangement and can advantageously influence the setting of the minimum NPO resistance and of the average NPO resistance. This applies analogously to the minimum leakage resistance and the average leakage resistance.

In some embodiments, a distal end face of the outer cone, terminating the outer cone and provided with the further opening, can protrude beyond a distal collar of the sleeve-shaped portion by a distance of at least 2.1 mm or at least 2.2 mm. In some embodiments, this distance is at most 2.5 mm or at most 2.4 mm. In some embodiments, the distal end face of the outer cone protrudes beyond a distal collar of the sleeve-shaped portion by a distance of 2.1 mm to 2.5 mm, such as of 2.2 mm to 2.4 mm, or of 2.3 mm. This structural adaptation can also advantageously influence the setting of the minimum NPO resistance and of the average NPO resistance. This applies analogously to the minimum leakage resistance and the average leakage resistance.

According to some embodiments, the syringe body can have, at the proximal end portion, an inner circumferential surface with a bevel that tapers the inner circumferential surface as viewed from the proximal end portion in the direction of the distal end portion. In other words, the inner circumferential surface in the region of the bevel can taper conically as viewed in the direction of the distal end portion. The bevel can make it easier to insert the piston rod arrangement, more specifically the piston, into the chamber of the syringe body. Viewed in the direction of the longitudinal axis of the syringe body, the bevel can have a length of at least 1.2 mm or at least 1.4 mm. In some embodiments, this length is at most 1.8 mm or at most 1.6 mm. In some embodiments, said length is between 1.2 mm and 1.8 mm, such as from 1.4 mm to 1.6 mm, or approximately 1.5 mm. Additionally or alternatively to this, the bevel can enclose an angle of at least 13°, such as of at least 14° or of at least 15°, with the longitudinal axis. By providing a bevel of such dimensions, the total length of the syringe body can be reduced in relation to known syringe bodies. This can have an advantageous effect on the ergonomics of the syringe body or its handling by the user. However, a bevel of such dimensions can ensure sufficient stability and leaktightness (container closure integrity (CCI)) of the syringe. For example, in a completely filled and non-actuated syringe, provision can be made that there is a distance of at least 9 mm to at most 10 mm, or approximately 9.5 mm, between the proximal syringe end and a proximal end of the piston of the piston rod arrangement.

In some embodiments, the syringe body can have a maximum total length of 80 mm and a chamber internal diameter of at most 5 mm, wherein a volume of at least 1 ml is receivable in the syringe body. To be more specific, a volume of at least 1 ml is receivable in the chamber and in an adjoining chamber portion formed by the outer cone. The total length can be measured from an end face of the syringe body delimiting the proximal end portion as far as an end face of the syringe body delimiting the distal end portion, i.e. the end face of the outer cone. The chamber internal diameter can be constant over the entire length of the chamber. For example, a volume of 1.073 ml is receivable in the chamber and the chamber portion together, in order to permit an overfill of 2% and the inclusion of an air bubble of 1 mm in length in the chamber. It should be noted that the receivable volume is not to be equated with the total volume formed by the entire chamber and the chamber portion. In addition to the volume of medium to be received, and to the above-described tolerances for the overfill and the air bubble, the chamber must be able, even in a non-actuation position, to receive a part of the piston rod arrangement and store the latter in a stable manner. For this purpose, the piston of the piston rod arrangement should, in a non-actuation position, be received in the syringe body at a point sufficiently far from the proximal end of the syringe body. For example, a distance of 9.5 mm can be provided between the proximal syringe end and a proximal end of the piston of the piston rod arrangement.

The syringe body can be configured and dimensioned within and according to ISO 11040-6:2012-04-01.

In some embodiments, the syringe body has a maximum total length of 60 mm and a chamber internal diameter of at most 4.65 mm, wherein a volume of at least 0.5 ml is receivable in the chamber and the chamber portion together.

In some embodiments, the syringe body has a maximum total length of 71 mm and a chamber internal diameter of at most 5 mm, wherein a volume of at least 0.8 ml is receivable in the chamber and the chamber portion together.

In some embodiments, the syringe body has a maximum total length of 95 mm and a chamber internal diameter of at most 6.45 mm, wherein a volume of at least 2.25 ml is receivable in the chamber and the chamber portion together.

In some embodiments, the syringe body has a maximum total length of 117 mm and a chamber internal diameter of at most 6.45 mm, wherein a volume of at least 2.8 ml is receivable in the chamber and the chamber portion together.

In some embodiments, the syringe body has a maximum total length of 56 mm and a chamber internal diameter of at most 12.2 mm, wherein a volume of at least 2.8 ml is receivable in the chamber and the chamber portion together.

In some embodiments, the syringe body has a maximum total length of 58 mm and a chamber internal diameter of at most 12.2 mm, wherein a volume of at least 3.0 ml is receivable in the chamber and the chamber portion together.

In some embodiments, the syringe body has a maximum total length of 115 mm and a chamber internal diameter of at most 8.75 mm, wherein a volume of at least 5 ml is receivable in the chamber and the chamber portion together.

The values described previously can be maximum dimensions or exact dimensions. A small chamber internal diameter has a positive effect on the application of a highly viscous liquid by a finger force exerted on the syringe or the injection device. At the same time, however, the chosen total length of the syringe body, on which the total length of the piston rod arrangement used therewith also depends, must not be too great, in order to ensure maneuverability. The previously described embodiments are illustrative embodiments which, for different syringe body volumes, indicate advantageous combinations of total length and internal diameter.

According to some embodiments, the syringe body can have, at least in the region of the chamber, a wall thickness of at least 1.7 mm, such as at least 1.8 mm, at least 2.0 mm, or at least 2.2 mm. Such a wall thickness can positively influence the dimensional stability of the syringe body during use and can thereby reduce mechanical failure of the syringe body. The indicated values represent an optimized geometry in terms of the ratio between internal diameter and external diameter.

In the region of the chamber, for example, the syringe body can have an external diameter of between 5 mm and 15 mm, such as of between 7.5 mm and 12.5 mm, of between 8.4 mm and 10 mm, or of approximately 9.4 mm.

The syringe body can be configured in such a way that it has an extrusion force of less than 40 N when a standard piston is moved at 10 mm/min in the chamber in the direction of the distal end portion. The syringe body can be configured in such a way that it has an extrusion force of less than 75 N when a standard piston is moved at 50 mm/min in the chamber in the direction of the distal end portion. The syringe body can be configured in such a way that it has an extrusion force of less than 100 N when a standard piston is moved at 100 mm/min in the chamber in the direction of the distal end portion. The previous values relate to the discharging of a highly viscous medium with a storage modulus G' of approximately 84.5 Pa and a loss factor tan δ of approximately 0.48. The viscosity can be measured with a plate/plate measurement system at 25° C. and an air pressure of 1013.25 hPa (e.g. the MCR 302 rheometer from the company Anton Paar), in particular with a frequency of 1 Hz. The measurement can be carried out, for example, by the method according to ISO 6721-10-2015-09. The extrusion force describes the force with which the medium emerges from a cannula of a needle arrangement which is connected to the syringe body. Highly viscous media generally require higher extrusion forces than low-viscosity media. The previous values apply to a test set-up with a needle arrangement which comprises a cannula with a thickness of 30 G and a length of 13 mm, i.e. a 30 G×½ needle arrangement, in particular the needle arrangement "TSK HYPODERMIC NEEDLE", ref. HPC-300131-320, 30 G×½. The cannula in this test procedure is open, such that the highly viscous medium can emerge from the cannula. The needle arrangement comprises, as Luer lock connector counterpiece, a thread (in contrast to the needle arrangement with fins). A syringe body with such comparatively low extrusion forces for highly viscous media requires less force to be applied by the user and permits improved dosing accuracy. Therefore, despite highly viscous media being used, such syringe bodies permit the use of needle arrangements having cannulas of low thickness, i.e. a thickness of 30 G or more.

In some embodiments, the syringe body can be produced from a plastics material which may have an elastic modulus of between 2800 MPa and 3300 MPa, such as of between 2900 MPa and 3200 MPa (1 mm/min, ISO 527 parts 1 and 2). The plastics material can have a tensile strength (5 mm/min, ISO 527 parts 1 and 2) of between 58 MPa and 65 MPa, such as in the region of 60 MPa to 63 MPa. The plastics material can have a water uptake of less than 0.01% (ISO 62). Moreover, the plastics material can have an indentation hardness of between 180 and 195 N/mm$^2$ (30-second value at a load of 961 N as per ISO 2039 part 1). The plastics material can have a softening point of between 120 and 180° C. (HDT/B 0.45 MPa, ISO 75 parts 1 and 2). The coefficient of linear thermal expansion of the plastics material can be $6.0 \times 10^{-4}$ K$^{-1}$ (ISO 11 359 parts 1 and 2). The elongation at break of the plastics material can be in the region of 2.5 to 2.7% (ISO 527 parts 1 and 2). The impact strength of the plastics material can be approximately 15 kJ/m$^2$ (ISO 179/1eU) and/or the notched impact strength can be in the region of 1.6 kJ/m$^2$ to 1.8 kJ/m$^2$ (ISO 179/1eA).

In some embodiments, the proximal end portion of the syringe body comprises a flange. The flange can form a handle, for supporting the index finger and middle finger of a user during use of the syringe body, or can be provided with such a handle.

A further aspect of the present invention provides a syringe for injecting a highly viscous medium, with a syringe body of the type described previously and with a piston rod arrangement. The piston rod arrangement comprises a piston rod and a piston mounted on a distal end of the piston rod. The piston is received in the chamber via the opening at the proximal end portion of the syringe body and is guided displaceably in the chamber. The piston can comprise three sealing lips, for example.

The syringe can comprise a highly viscous medium received in the chamber of the syringe body. In some embodiments, the highly viscous medium is characterized by a storage modulus G' of at least 30 Pa and at most 150 Pa, such as at least 50 Pa and at most 100 Pa, or at least 70 Pa and at most 90 Pa. The loss factor tan δ can be between 0.2 and 0.8, such as between 0.3 and 0.6 or between 0.4 and 0.5. The viscosity can be measured with a plate/plate measurement system at 25° C. and an air pressure of 1013.25 hPa (e.g. the MCR 302 rheometer from the company Anton Paar), in particular with a frequency of 1 Hz. The measurement can be carried out, for example, by the method according to ISO 6721-10-2015-09. For example, the syringe can comprise hyaluronic acid filler and/or other cosmetic preparations received in the chamber of the syringe body.

The syringe can have a gripping length of between 6 cm and 12 cm, such as of between 7.5 cm and 8 cm. The gripping length denotes the length between the proximal end of the syringe body and a proximal end of the piston rod arrangement. The piston rod arrangement can be provided with a handle at the proximal end.

A further aspect of the present invention provides an injection device for injecting a highly viscous medium, comprising a syringe of the type described previously and a needle arrangement. The needle arrangement comprises a needle hub and a cannula, wherein the needle hub, for producing the Luer lock connection between the syringe body and the needle arrangement, has a Luer lock connector counterpiece that complements the Luer lock connector of the syringe body. Accordingly, the needle hub comprises an inner cone complementing the outer cone of the syringe body, and, in some embodiments, an outer thread which complements the inner thread of the syringe body. As an alternative to an outer thread, the needle hub can comprise two fins arranged on the outer circumference of the needle hub.

The needle arrangement can comprise a cannula with a thickness of at least 30 G (gauge), such as at least 31 G, at least 32 G, at least 33 G, at least 34 G, or at least 35 G. The cannula can have a length of at least 10 mm, such as at least 11 mm, at least 12 mm, or at least 13 mm. Alternatively, the cannula can have a length of 25 mm or more.

The needle hub of the needle arrangement can comprise an inner cone which, along a longitudinal axis of the needle arrangement, has a length of between 3 mm and 7 mm, such as of between 5.5 mm and 6.5 mm, or of 6.1 mm.

In some embodiments, the injection device can comprise the needle arrangement "TSK HYPODERMIC NEEDLE", ref. HPC-300131-320, 30 G×½, or a needle arrangement comparable thereto.

Alternatively, the injection device can comprise the needle arrangement "TSK STERiJECT Hypodermic Needle", ref. PRC-300131, 30 G×½, or a needle arrangement comparable thereto.

In some embodiments, the syringe body is made of a plastics material which comprises or consists of a cyclic olefin copolymer (COC) and/or a cyclic olefin polymer (COP).

In some embodiments, the plastics material comprises one or more additives, wherein one additive can be a dye.

Although some aspects and features are described previously and further herein in relation to the syringe body, these aspects and features can apply accordingly to the syringe and/or the injection device described herein, and vice versa.

Exemplary embodiments provided according to the present invention also provide a therapeutic or cosmetic procedure comprising applying a highly viscous cosmetic preparation using a syringe body as described herein, a syringe as described herein, or an injection device as described herein. In some embodiments, the highly viscous medium is characterized by a storage modulus G' of at least 30 Pa and at most 150 Pa, such as at least 50 Pa and at most 100 Pa, or at least 70 Pa and at most 90 Pa. The loss factor tan δ can be between 0.2 and 0.8, such as between 0.3 and 0.6 or between 0.4 and 0.5. The viscosity can be measured with a plate/plate measurement system at 25° C. and an air pressure of 1013.25 hPa (e.g. the MCR 302 rheometer from the company Anton Paar), in particular with a frequency of 1 Hz. The measurement can be carried out, for example, by the method according to ISO 6721-10-2015-09. The application can involve injecting the cosmetic preparation into an organism to be treated. In some embodiments, the preparation is applied to an application site of a human organism. The application can be a subcutaneous injection. The application site can be a human face or a region thereof.

Referring now to the drawings, FIG. 1 illustrates various perspective views of an exemplary embodiment of an injection device 10 provided according to the present invention, in exploded views and in the assembled state. The injection device 10 comprises a syringe body 12, a piston rod arrangement 14 and a needle arrangement 16.

The elongate syringe body 12 has a hollow cylindrical configuration and forms a chamber for receiving a medium, in particular a highly viscous medium. The syringe body 12 has a distal end portion 18 and a proximal end portion 20. The proximal end portion 20 has an opening through which the piston rod arrangement 14 is insertable into the chamber (see views on the right in FIG. 1). At the distal end portion 18 of the syringe body 12, a Luer lock connector 22 is formed, which is described in detail with reference to FIG. 2. The proximal end portion 20 of the syringe body 12 is provided with a flange 24, which serves as a handle for supporting the index finger and middle finger of a user during use of the syringe body 12.

The piston rod arrangement 14 comprises a piston rod 26 and a piston 28 which, in the illustrated embodiment, is produced from an elastic material and has three sealing lips. The piston 28 is mounted at a distal end of the piston rod 26 and can be guided slidably in the chamber, via an inner circumferential surface of the chamber of the syringe body 12, and is displaceable in the direction of a longitudinal axis of the chamber. At a proximal end, the piston rod arrangement 14 comprises a handle 30 via which force can be applied to the injection device 10 by a thumb of the user.

The needle arrangement 16 comprises a needle hub 32 and a cannula 34 in the form of a hollow needle. In the illustrated embodiment, the cannula 34 has a thickness of at least 30 G and a length of 13 mm. However, cannulas with other dimensions can also be used. The needle hub 32 has a Luer lock connector counterpiece 36 which, with the Luer lock connector 22 of the syringe body 12, can produce a tight Luer lock connection in order to connect the syringe body 12 to the needle arrangement 16. In the illustrated embodiment, the Luer lock connector counterpiece 36, more precisely the needle hub 32, comprises an inner cone, and two fins formed on an outer circumferential surface of a proximal end of the needle hub 32. It will be appreciated that, in some embodiments, the needle hub can be provided with an outer thread, or an outer thread portion, instead of fins. By such an embodiment with an outer thread, a still more secure Luer lock connection can be realized.

In order to close the syringe body 12, for example during transport, the latter can be closed in the region of the Luer lock connector 22 by the cover 38 shown in FIG. 1. This cover 38 is designed to complement the Luer lock connector 22 of the syringe body 12. The cover 38 is removed from the syringe body 12 before the needle arrangement 16 is connected to the syringe body 12.

In the assembled state in which the syringe body 12, the piston rod arrangement 14 and the needle arrangement 16 are structurally connected and operatively connected to one another, the injection device 10 can be brought from a non-actuation position to an actuation position, by the piston 28 being moved inside the chamber from the proximal end portion 20 in the direction of the distal end portion 18. In this way, a highly viscous medium received in the chamber, for example hyaluronic acid, can be injected through the cannula 34 under the surface of a patient's skin.

In the illustrated embodiment, the syringe body 12 is produced from cyclic olefin polymer (COP) or from cyclic olefin copolymer (COC).

FIG. 2 illustrates an enlarged sectional view of the Luer lock connector 22 of the syringe body 12. The Luer lock connector 22 comprises an outer cone 40 with a further opening 42 for dispensing the highly viscous medium received in the chamber. As can be seen from FIGS. 1 and 2, the outer cone 40 protrudes as a conically shaped nozzle beyond a distal end of the syringe body 12. The Luer lock connector 22 moreover comprises a sleeve-shaped portion 44, which is provided with an inner thread 46. The outer cone 40 is surrounded by the sleeve-shaped portion 44, wherein the outer cone 40 and the sleeve-shaped portion 44 are arranged coaxially to each other.

The inner thread 46 has a smallest internal diameter $I_1$ of 7.1 mm, measured from thread crest 50 to opposite thread crest 50' of the inner thread 46. The greatest internal diameter $I_2$, measured from thread root 54 to opposite thread root 54' of the inner thread 46, is 8.0 mm in the illustrated embodiment. The external diameter $A_H$ of the sleeve-shaped portion 44 is 10.0 mm. Accordingly, the sleeve-shaped portion 44 has a wall thickness of 1 mm.

As can be seen from FIG. 2 and from the detail of the thread profile of the inner thread 46 in FIG. 3, the inner thread 46 has a breadth $B_K$ of 0.48 mm at the crest 50 of the thread profile. Moreover, the inner thread 46 has a breadth $B_G$ of 0.9 mm at the root 54 of the thread profile. On both sides of the thread profile, the inner thread has an angle α and β, in each case of 25°. A thread profile with these dimensions serves to optimize the common contact face with the complementary outer thread of the associated needle arrangement. This can contribute to the specific setting of the minimum NPO resistance, the average NPO resistance, the minimum leakage resistance and the average leakage resistance.

The outer cone 40 comprises a distal end face 56, in which the further opening 42 is formed. Viewed in the direction of the longitudinal axis L of the syringe body 12, the distal end face 56 protrudes beyond a distal collar 58 of the sleeve-shaped portion 44 by a distance A of 2.3 mm. Moreover, the distal end face 56 of the outer cone 40 is spaced apart by a distance B of 3.1 mm from an underside of the first complete thread profile facing away from the end face 56. In the illustrated embodiment, the outer cone 40 has a total cone length of 8.9 mm.

The parameters shown in FIG. 3, namely $B_K$, $B_G$, α and β of the thread profile, smallest internal diameter $I_1$ and/or distance A, can be provided with these dimensions in syringe bodies having different chamber volumes, in order to achieve optimal values for the minimum NPO resistance, for the average NPO resistance, for the minimum leakage resistance and for the average leakage resistance of the syringe body 12.

FIG. 4 illustrates a sectional view of the syringe body 12 with a piston rod arrangement 14 received therein. For reasons of clarity, the piston rod arrangement 14 is not shown in its entirety. The syringe body 12 in the illustrated embodiment has a total length $L_{SK}$ of 80.0 mm. The total length $L_{SK}$ is made up of the length of a portion of the syringe body, forming the chamber, and of the total cone length C of the outer cone 40 together. The chamber internal diameter $I_K$ is 5 mm in the example shown. Therefore, a medium, in particular a highly viscous medium, with a volume V of 1073 mm$^3$ can be received in the chamber of the syringe body 12 and in the adjoining chamber portion formed by the outer cone 40. This receivable volume V derives from the considerations and resulting design measures according to which the syringe body 12 is intended to make available a highly viscous medium of 1 ml in volume. Moreover, the chamber must permit an overfill of 2% and inclusion of an air bubble of 1 mm in length (see length s). In addition to the volume of medium to be received, and to the previously described tolerances for the overfill and the air bubble, the chamber must be able, even in the non-actuation position, to receive a part of the piston rod arrangement and store the latter in a stable manner. For this purpose, a proximal end of the piston 28 of the piston rod arrangement 14 should be spaced apart from the proximal end of the syringe body 12 by a distance u of 9.5 mm in a non-actuation position. Moreover, a third (proximal) sealing lip of the piston 28 of the piston rod arrangement 14 is spaced apart from a bevel 60 of the syringe body 12 by a distance o, likewise of 9.5 mm, in this non-actuation position. The piston 28 has a length t of, for example, 6.9 mm.

The bevel 60 is formed on the inner circumferential surface of the proximal end portion 20 of the syringe body 12. The bevel 60 tapers the inner circumferential surface of the syringe body 12 as viewed from the proximal end portion 20 in the direction of the distal end portion 18.

Figure 5:
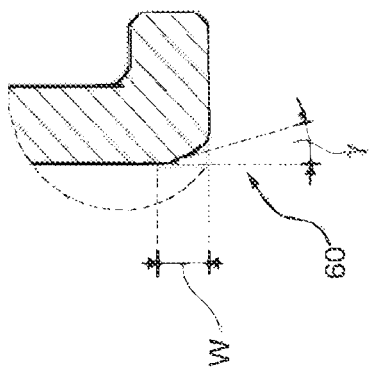
FIG. 5 illustrates a detail of a bevel of the syringe body of FIG. 4.

The bevel 60 is illustrated enlarged in FIG. 5. Viewed in the direction of a longitudinal axis L of the syringe body 12, it has a length w of 1.5 mm, and it encloses an angle γ of 15° with the longitudinal axis L. A radius R of 0.5 mm is provided in a transition region of the bevel 60 to the proximal end of the syringe body 12.

In the region of the chamber, the syringe body 12 in the illustrated embodiment has a wall thickness of 2.2 mm, which serves to provide sufficient stability against breakage of the syringe body.

Figure 6:
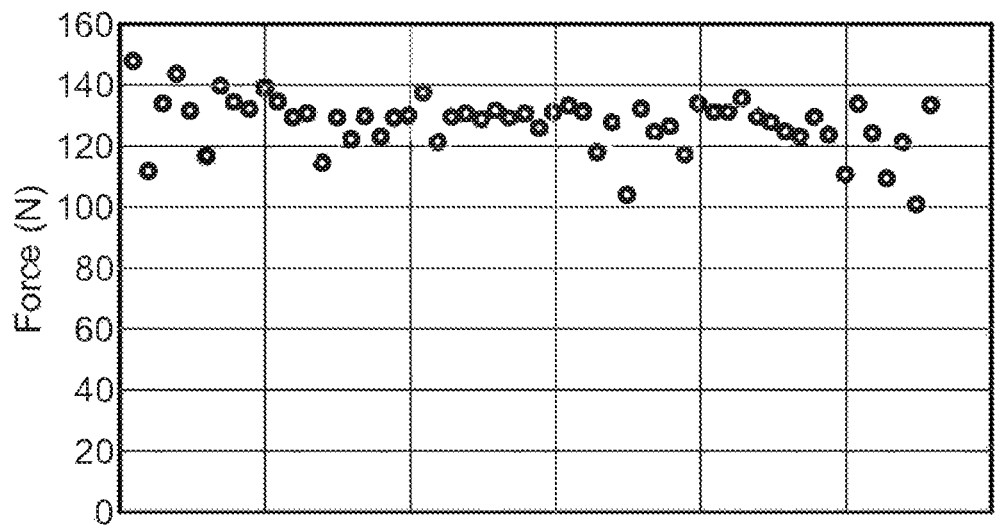
FIG. 6 illustrates a diagram with test results for a syringe body provided according to the present invention with respect to NPO and leakage.

FIG. 6 illustrates a diagram with test results for a syringe body provided according to the present invention, which indicate different measured resistances of the syringe body to NPO and leakage. The tests on which the results are based were carried out with the syringe body 12 of FIGS. 1 to 5. The various measurements of the depicted measurement series (56 individual measurements) are plotted in the direction of the x axis. The y axis indicates the measured force that was applied to the syringe at the time of failure of the syringe body due to NPO or leakage.

For the test procedure, the syringe body 12 to be tested was arranged vertically in the universal testing machine "TesT 106.2 kN" from the company TesT and held in the region of the proximal end of the syringe body 12. Before the start of the test, the tested syringe body 12 was connected via the Luer lock connector 22 to the needle arrangement "TSK STERiJECT Hypodermic Needle", ref.: PRC-300131, 30 G×½ which, in order to produce the Luer lock connection, has as Luer lock connector counterpiece an inner cone and two fins arranged on an outer circumference of a needle hub of the needle arrangement. The Luer lock connector 22 of the syringe body 12 was screwed onto the Luer lock connector counterpiece of the needle arrangement with a torque of 12 Ncm. Before the test was carried out, the cannula of the needle arrangement, which has a thickness of 30 G and a length of 13 mm (30 G×½), was flattened by a hammer and thereby closed. For the test procedure, a dry Luer lock connection was produced by screwing the needle arrangement onto the syringe body before then introducing a highly viscous medium into the chamber. The test procedure was carried out with non-steam-sterilized components (syringe body, needle arrangement, piston rod arrangement). A highly viscous placebo medium was used for the present test procedure. The highly viscous placebo medium had a storage modulus G' of approximately 84.5 Pa and a loss factor tan δ of approximately 0.48. The viscosity was measured with a plate/plate measurement system at 25° C. and an air pressure of 1013.25 hPa (e.g. the MCR 302 rheometer from the company Anton Paar). The frequency was 1 Hz. The measurement was carried out according to ISO 6721-10-2015-09. The tested syringe body 12 was filled completely with this material, i.e. with a volume of 1073 mm$^3$. A standard piston of the FM257 type from the manufacturer Daetwyler was used for the piston arrangement.

By way of a test punch of the testing machine, a force was applied vertically to the proximal end of the piston rod arrangement. The test punch was moved at a constant test speed of 12.6 mm/min in the direction of the distal end portion of the syringe body. The force acting on the piston rod arrangement was increased continuously. The maximum force set was a force of 420 N, at which the test would have been discontinued. The acting force was detected by a force sensor at a scanning rate of 200 Hz. The test punch was moved continuously until leakage and/or NPO was detected, i.e. until the measured force dropped suddenly by at least 30%.

The acting force at the time of occurrence of leakage and/or NPO was documented for each measurement and entered in the diagram shown in FIG. 6. The diagram of FIG. 6 shows the results of a measurement series comprising 56 measurements. The results presented in the diagram show that for none of the 56 measurements did the syringe body fail due to NPO or leakage at a force of 100 N. Carrying out a total of 56 measurements ensures that it is possible to determine a minimum NPO resistance, which is defined as meaning that, below this threshold value, needle pop-off occurs in not more than 1.8% of the tested syringe bodies.

Since the maximum finger force with which syringes are in practice actuated is on average 95 N, the occurrence of NPO and/or leakage can be avoided with the syringe body provided according to the present invention.

Figure 7:
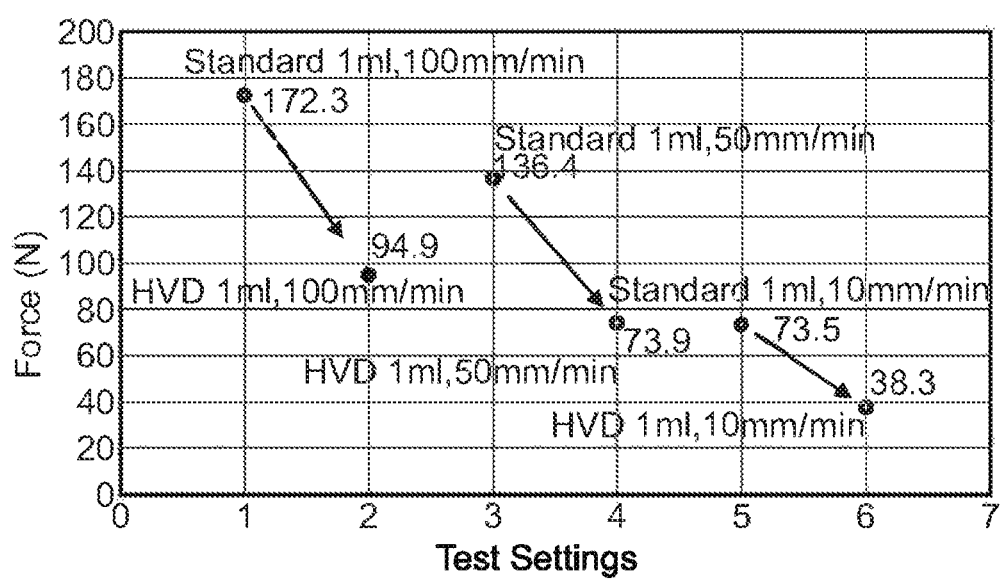
FIG. 7 illustrates a diagram with test results for a syringe body provided according to the present invention with respect to extrusion forces.

FIG. 7 shows a further diagram indicating test results for extrusion forces of a syringe body provided according to the present invention compared to extrusion forces of a known product from the prior art. The various measurements are plotted on the x axis of the diagram. The y axis indicates the measured extrusion force. The diagram shows measurements at three different test speeds.

A syringe body provided according to the illustrated embodiment of FIGS. 1 to 5 was compared with a "SCHOTT COC Standard" syringe body with a 1-ml filling volume (name "TopPac 1 ml long"). For the piston arrangement, a standard piston of the type FM257 from the manufacturer Daetwyler was used with both syringe bodies. The needle arrangement used for both syringe bodies was the "TSK HYPODERMIC NEEDLE", ref. HPC-300131-320, 30 G×½, with an open (unflattened) cannula having a thickness of 30 G and a length of 13 mm. A highly viscous medium was used as extruded medium. The highly viscous medium had a storage modulus G' of approximately 84.5 Pa and a loss factor tan δ of approximately 0.48. The viscosity was measured with a plate/plate measurement system at 25° C. and an air pressure of 1013.25 hPa (e.g. the MCR 302 rheometer from the company Anton Paar). The frequency was 1 Hz. The measurement was carried out according to ISO 6721-10-2015-09.

Testing was carried out with test speeds of 100 mm/min, 50 mm/min and 10 mm/min, at which speeds the piston was moved in the syringe body from the proximal end to the distal end. The test results show that, at a test speed of 100 mm/min, the extrusion force of the syringe body provided according to the present invention was reduced from 172.3 N to 94.9 N compared to the syringe body from the prior art. Moreover, the test results show that, at a test speed of 50 mm/min, the extrusion force of the syringe body provided according to the present invention was reduced from 136.4 N to 73.9 N compared to the syringe body from the prior art. Furthermore, the test results show that, at a test speed of 10 mm/min, the extrusion force of the syringe body provided according to the present invention was reduced from 73.5 N to 38.3 N compared to the syringe body from the prior art.

The extrusion forces of the syringe body 12 provided according to the present invention are therefore significantly lower than the extrusion forces of known syringe bodies. The syringe body provided according to the present invention therefore requires less force to be applied by the user in order to dispense highly viscous media and thereby permits an improved dosing accuracy. Therefore, despite highly viscous media being used, the syringe bodies provided according to the present invention permit the use of needle arrangements having cannulas of low thickness, i.e. a thickness of 30 G or more.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS 10 injection device
12 syringe body
14 piston rod arrangement
16 needle arrangement
18 distal end portion
20 proximal end portion
22 Luer lock connector
24 flange
26 piston rod
28 piston
30 handle
32 needle hub
34 cannula
36 fin
38 cover
40 outer cone
42 opening
44 sleeve-shaped portion
46 inner thread
50, 50' crest
54, 54' root
56 end face
58 distal collar
60 bevel
L longitudinal axis
A distance
B distance
C total length of cone
$I_1$ smallest internal diameter
$I_2$ greatest internal diameter
$A_H$ external diameter
$B_K$ breadth of crest
$B_G$ breadth of root
α angle at the thread profile
β further angle at the thread profile
γ angle of the bevel
$I_K$ chamber internal diameter
V receivable volume
$L_{SK}$ total length
distance
s length of the air bubble
t piston length
u distance
w length of the bevel

What is claimed is:

1. A syringe body for a syringe for injecting a highly viscous medium, the syringe body having a hollow cylindrical configuration and forming a chamber configured to receive the highly viscous medium, the syringe body comprising:
   a distal end portion;
   a proximal end portion having an opening through which a piston rod arrangement is insertable into the chamber;
   a Luer lock connector formed at the distal end portion, the Luer lock connector comprising an outer cone with a further opening configured to dispense the highly viscous medium and a sleeve-shaped portion with an inner thread, the syringe body having a minimum needle pop-off (NPO) resistance of over 90 N, wherein the inner thread has a smallest internal diameter of between 7.05 mm and 7.15 mm, wherein the inner thread, at a crest of a thread profile of the inner thread, has a breadth of between 0.44 mm and 0.52 mm, and wherein the inner thread, at a root of the thread profile, has a breadth of between 0.85 mm and 0.95 mm; and
   a needle hub coupled to the Luer lock connector and carrying a cannula, the needle hub comprising an inner chamber that is fluidly coupled with the further opening and a projection extending into the inner chamber that fluidly couples the cannula to the inner chamber.

2. The syringe body of claim 1, wherein the syringe body has an average NPO resistance of at least 100 N.

3. The syringe body of claim 1, wherein a distal end face of the outer cone protrudes beyond a distal collar of the sleeve-shaped portion by a distance of 2.1 mm to 2.5 mm.

4. The syringe body of claim 1, further comprising an inner circumferential surface at the proximal end portion, the inner circumferential surface having a bevel that tapers the inner circumferential surface as viewed from the proximal end portion in a direction of the distal end portion, wherein the bevel has a length of between 1.2 mm and 1.8 mm, viewed in a direction of a longitudinal axis of the syringe body, and/or encloses an angle of at least 13° with the longitudinal axis.

5. The syringe body of claim 1, wherein the syringe body has a maximum total length of 80 mm and a chamber internal diameter of at most 5 mm, wherein a volume of at least 1 ml is receivable in the syringe body.

6. The syringe body of claim 1, wherein the syringe body has, at least in a region of the chamber, a wall thickness of at least 1.7 mm.

7. The syringe body of claim 1, wherein the syringe body is produced from a plastics material that has an elastic modulus of between 2800 MPa and 3300 MPa.

8. The syringe body of claim 1, wherein the minimum NPO resistance of the syringe body is between 90 N and 105 N.

9. An injection device, comprising:
a syringe body having a hollow cylindrical configuration and forming a chamber configured to receive a highly viscous medium, the syringe body comprising:
a distal end portion;
a proximal end portion having an opening; and
a Luer lock connector formed at the distal end portion, the Luer lock connector comprising an outer cone with a further opening configured to dispense the highly viscous medium and a sleeve-shaped portion with an inner thread, the syringe body having a minimum needle pop-off (NPO) resistance of over 90 N, wherein the inner thread has a smallest internal diameter of between 7.05 mm and 7.15 mm, wherein the inner thread, at a crest of a thread profile of the inner thread, has a breadth of between 0.44 mm and 0.52 mm, and wherein the inner thread, at a root of the thread profile, has a breadth of between 0.85 mm and 0.95 mm; and
a needle arrangement comprising a needle hub coupled to the Luer lock connector and carrying a cannula, the needle hub comprising an inner chamber that is fluidly coupled with the further opening and a projection extending into the inner chamber that fluidly couples the cannula to the inner chamber; and
a piston rod arrangement comprising a piston rod and a piston mounted on a distal end of the piston rod, received in the chamber via the opening at the proximal end portion of the syringe body, and guided displaceably in the chamber.

10. The injection device of claim 9, wherein the needle hub has a Luer lock connector counterpiece that complements the Luer lock connector of the syringe body and is configured to produce a Luer lock connection between the syringe body and the needle arrangement.

11. The injection device of claim 10, wherein at least one of:
the cannula has a thickness of at least 31 G; or
the needle hub comprises an inner cone which, along a longitudinal axis of the needle arrangement, has a length of between 3 mm and 7 mm.

12. The injection device of claim 11, wherein the highly viscous medium comprises hyaluronic acid.

13. The injection device of claim 9, further comprising a highly viscous medium received in the chamber.

14. The injection device of claim 9, wherein the syringe body has an average NPO resistance of at least 100 N.

15. The injection device of claim 9, wherein the minimum NPO resistance of the syringe body is between 90 N and 105 N.

16. A method for performing a cosmetic procedure, the method comprising:
applying a highly viscous cosmetic preparation to a patient using an injection device, the injection device comprising:
a syringe body having a hollow cylindrical configuration and forming a chamber holding the highly viscous cosmetic preparation, the syringe body comprising:
a distal end portion;
a proximal end portion having an opening;
a Luer lock connector formed at the distal end portion, the Luer lock connector comprising an outer cone with a further opening configured to dispense the highly viscous cosmetic preparation and a sleeve-shaped portion with an inner thread, the syringe body having a minimum needle pop-off (NPO) resistance of over 90 N, wherein the inner thread has a smallest internal diameter of between 7.05 mm and 7.15 mm, wherein the inner thread, at a crest of a thread profile of the inner thread, has a breadth of between 0.44 mm and 0.52 mm, and wherein the inner thread, at a root of the thread profile, has a breadth of between 0.85 mm and 0.95 mm; and
a needle hub coupled to the Luer lock connector and carrying a cannula, the needle hub comprising an inner chamber that is fluidly coupled with the further opening and a projection extending into the inner chamber that fluidly couples the cannula to the inner chamber; and
a piston rod arrangement comprising a piston rod and a piston mounted on a distal end of the piston rod, received in the chamber via the opening at the proximal end portion of the syringe body, and guided displaceably in the chamber.

17. The method of claim 16, wherein the highly viscous cosmetic preparation comprises hyaluronic acid.

* * * * *